United States Patent [19]
Takishita

[11] Patent Number: 5,042,305
[45] Date of Patent: Aug. 27, 1991

[54] ULTRASONIC FLAW DETECTING SYSTEM
[75] Inventor: Yoshihiko Takishita, Ibaraki, Japan
[73] Assignee: Hitachi Construction Machinery Co., Ltd., Tokyo, Japan
[21] Appl. No.: 385,458
[22] Filed: Jul. 26, 1989
[30] Foreign Application Priority Data
  Jul. 30, 1988 [JP] Japan ............... 63-189581
[51] Int. Cl.[5] ............................. G01N 29/00
[52] U.S. Cl. ..................................... 73/625
[58] Field of Search ............... 73/619, 620, 621, 625, 73/628, 633, 602, 634

[56] References Cited
U.S. PATENT DOCUMENTS

| 3,575,042 | 4/1968 | Lovelace et al. | 73/620 |
|---|---|---|---|
| 4,213,183 | 7/1980 | Barron et al. | 73/634 |
| 4,381,787 | 5/1983 | Hottinger | 73/620 |
| 4,481,822 | 11/1984 | Kubota et al. | 73/625 |
| 4,664,122 | 5/1987 | Yano | 128/660 |

FOREIGN PATENT DOCUMENTS
0114596 8/1984 European Pat. Off.
0189137 7/1986 European Pat. Off.

OTHER PUBLICATIONS
"Method for Correcting Ultrasonic Flaw Detection Image", by Otsuka, Pat. Abstracts of Japan, vol. 12, No. 25, Jan. 1988.

Primary Examiner—Hezron E. Williams
Assistant Examiner—Louis M. Arana
Attorney, Agent, or Firm—Antonelli, Terry, Stout & Kraus

[57] ABSTRACT

According to the present invention, a cursor is displayed on a screen of display of an ultrasonic image obtained by scanning the surface of an inspection object by use of a probe formed by arrangement of array elements and, further, the cursor is moved to a desired position of the ultrasonic image so that ultrasonic waves are emitted to a position of the surface of the object corresponding to the aforementioned position and the reflection wave signals are displayed in another display portion. Accordingly, not only ultrasonic flaw detection (C-scope) in a plane of the object can be conducted, but also ultrasonic flaw detection (B-scope) in the direction of depth in a desired position of the object can be conducted simultaneously. Consequently, detailed flaw information, such as a flaw type, a flaw position, a flaw size and a flaw shape, in the object can be detected quickly.

7 Claims, 17 Drawing Sheets

F I G. 10
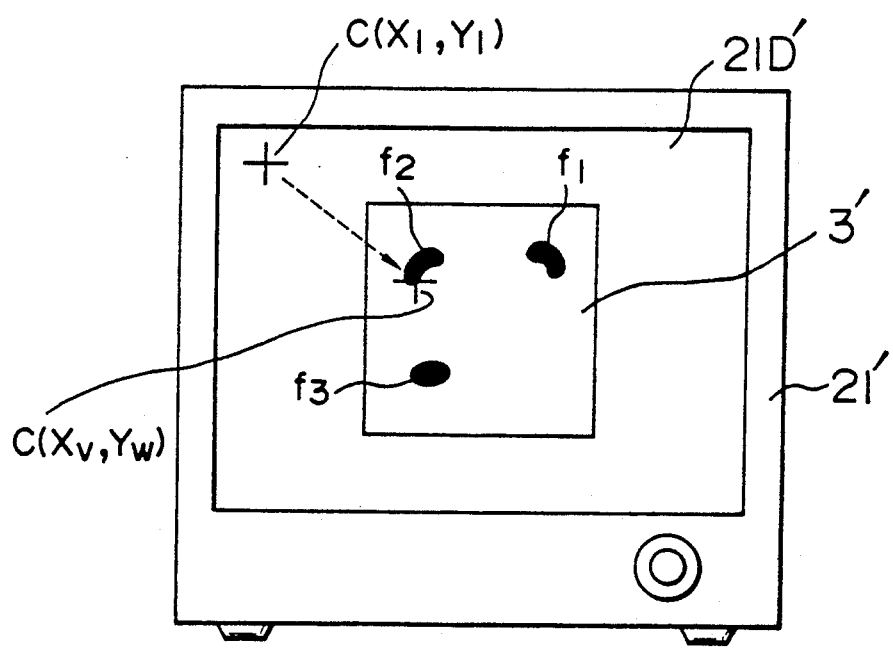

TIME

ULTRASONIC FLAW DETECTING SYSTEM

BACKGROUND OF THE INVENTION

The present invention relates to a ultrasonic flaw detecting system for detecting flaws in an object to be inspected by use of a an ultrasonic wave, and, more particularly, relates to a an ultrasonic flaw detecting system which is suitable for detecting, in detail and quickly, internal flaw conditions of an object to be examined.

A supersonic flaw detecting system has been used in various fields for the purpose of detecting internal flaws of an object to be inspected without destruction. In most cases, existence of internal flaws of an object to be inspected is checked within a predetermined range of the object. In such cases, the aforementioned range of the surface of the object is scanned by a probe to conduct flaw detection. As the probe, an array probe constituted by a large number of piezoelectric elements arranged linearly has been put into practical use, for example, as described in the paper by J. Kubota et al., entitled "High Speed Ultrasonic Image of IC Package". A supersonic flaw detecting system using such an array probe will be described hereunder.

FIG. 1 is a perspective view of a scanner portion of the supersonic flaw detecting system, and FIGS. 2A and 2B are a plan view and a side view of the array probe, respectively. In the drawings, the reference numeral 1 designates a flaw-detection water tank, 2 water put into the water tank 1, and 3 an object to be inspected mounted on the bottom surface of the water tank 1. The reference numeral 4 generally designates a scanner portion constituted by the following parts. The reference numeral 5 designates a scanner base for mounting the water tank 1 thereon, 6 a pair of frames fixed to the scanner base 5, 7 an arm disposed between the frames 6, 8 a holder disposed on the arm 7, 9 a pole attached to the holder 8, and 10 an array probe. The pair of frames 6 can drive the arm 7 in the Y-axis direction by a mechanism not shown. The arm 7 can drive the holder 8 in the X-axis direction by a mechanism not shown. The holder 8 and the pole 9 can cooperate to drive the array probe in the Z-axis direction (the direction orthogonal to the X- and Y-axes) by a mechanism not shown.

The array probe 10 has a configuration in which a large number of piezoelectric elements (hereinafter referred to as "array elements") are arranged linearly in the X-axis direction. When a pulse is given to each array element, the array element emits a supersonic wave and converts the reflected ultrasonic wave into an electric signal proportional thereto. In FIGS. 2A and 2B, the array elements are designated by numerals $10_1$ to $10_n$, respectively. In the drawings, black spots represent sampling points, YP represents a Y-axis direction sampling pitch, XP represents an X-axis direction sampling pitch, and AP represents an array element pitch in the array elements $10_1$ to $10_n$. The reference numeral 11 designates a package for packing the array probe 10 and the like therein.

The outline of the function of the array probe 10 will be described with reference to FIGS. 3A and 3B. In FIG. 3A, $T_1$ to $T_9$ represent array elements arranged linearly, $D_1$ to $D_9$ represent delay elements connected to the array elements $10_1$ to $10_9$, and p represents an excitation pulse received by each of the array elements $T_1$ to $T_9$. Two delay elements $D_1$ and $D_9$ are established to have an equal delay period. Similarly, two delay elements $D_2$ and $D_6$, two delay elements $D_3$ and $D_7$, and two delay elements $D_2$ and $D_6$ are established to have equal delay periods ($t_{28}$), ($t_{37}$), and ($t_{46}$), respectively. When the delay period of the delay element $D_5$ is represented by $t_5$, the delay periods thus established satisfy the following relation.

$$t_{19} < t_{28} < t_{37} < t_{46} < t_5 \ldots \quad (1)$$

Assuming now that the delay periods of the delay elements $D_1$ to $D_9$ are set to predetermined values according to the relation (1) and are supplied with excitation pulses p, then supersonic waves are emitted from the array elements $T_1$ to $T_9$ corresponding to the set delay periods. Accordingly, the supersonic waves emitted from the two array elements $T_1$ and $T_9$ are earliest and the supersonic wave emitted from the array element $T_5$ is last. The ultrasonic waves thus emitted from the array elements are propagated radiately, so that there occurs a point where the maximum values of amplitude of the ultrasonic waves coincide with each other. This point is represented by the symbol B in FIG. 3A. Because the magnitude of supersonic wave at this point B is far larger than the magnitude of ultrasonic wave at another point, the supersonic waves emitted from the array elements $T_1$ to $T_9$ are in such a state that they are converged into the point B as shown in the broken line. In other words, if suitable delay periods are given to the ultrasonic waves emitted from the array elements arranged linearly, an effect that the supersonic waves are converged into the point B can be attained. Hereinafter, this point B is referred to as a "focal point". If the delay periods are set to be respectively smaller than the aforementioned delay periods while the relation (1) is satisfied, the focal point B is shifted to a focal point B' which is longer as shown in the dot-and-dash line. Accordingly, the position of the focal point can be selected by adjusting the delay periods of the delay elements $D_1$ to $D_9$ as described above. In the case where this way is adapted to detection of a flaw in the object 3, the depth of flaw detection can be selected.

FIG. 3B is a view for explaining the function of the array probe 10 as shown in FIGS. 2A and 2B. In the drawing, the reference numerals $10_1$ to $10_n$ designate array elements which are the same as in FIG. 2A. Delay elements not shown are connected to the array elements $10_1$ to $10_n$, respectively. In the example of FIG. 3B, a number, m, of array elements $10_1$ to $10_m$ are selected so that supersonic waves emitted therefrom are apparently converged into a focal point $B_1$ in the same manner as described above by setting the delay periods suitably. This focal point $B_1$ is represented by the symbol $B_1$ in the FIG. 3B. Then, the array elements are shifted by one so that delay periods having the same pattern as the delay periods given to the array elements $10_1$ to $10_m$ are given to newly selected array elements $10_2$ to $1_{m+1}$. The focal point thus obtained is represented by the symbol $B_2$. Similarly, the array elements are shifted one by one and, lastly, array elements $10_{n-m+1}$ to $10_n$ are selected so that delay periods having the same pattern are given to the array elements, thus to obtain a focal point $B_{n-m+1}$. By the aforementioned procedure, flaw-detection scanning from the focal point $B_1$ to the focal point $B_{n-m+1}$ by the array probe 10 can be conducted consequently. In FIG. 3B, AP represents an element pitch of the probe, and SP represents a sampling pitch. Although FIG. 3B shows the case where AP is equal to SP, the values of AP and SP may be established by use of known electronic control means to satisfy the equation $SP=(\frac{1}{2})AP$ or $SP=(\frac{1}{4})AP$.

Although the description of delay periods by reference to FIGS. 3A and 3B has been applied to the case where ultrasonic waves are transmitted from the array elements, it is a matter of course that similar delay periods are required to be given to the array elements in the case where the ultrasonic waves reflected from the object are received by the array elements.

In the following, a control circuit in the supersonic flaw detecting system using the array probe is described. FIG. 4 is a block diagram of the control circuit. In FIG. 4 the reference numeral 10 designates an array probe as described above, 7M a motor for driving the arm 7 in the Y-axis direction, 8M a motor for driving the holder 8 in the X-axis direction, 7E an encoder for generating a driving signal to be given to the motor 7M and for detecting the amount of rotations of the motor 7M, and 8E an encoder for generating a driving signal to be given to the motor 8M and for detecting the amount of rotations of the motor 8M. The reference numeral 20 designates a signal processor comprising a CPU (central processing unit) 20a, an image L memory 20b for image processing, an interface 20c for input-output between the signal processor 20 and a certain external circuit, and a keyboard 20d. The signal processor 20 further has other elements such as RAM and ROM, the other elements being not shown. The reference numeral 21 designates a display unit.

The reference numeral 22 designates a delay period control circuit for controlling, under orders of the CPU 20a, delay periods which have been described with reference to FIGS. 3A and 3B. The reference numeral 23 designates pulsers for generating the excitation pulses p. In this example, a plurality of pulsers 23 are provided corresponding to the array elements. The reference numeral 24 designates a pulser-amplifier switching circuit for selectively switching the pulsers 23 in accordance with the instructions from the CPU 20a. The details of the pulser-amplifier switching circuit 24 will be described later. The reference numeral 25 designates AND circuits, and 26 amplifiers for reception and amplification of reflected wave signals of the ultrasonic waves emitted from the array elements. The AND circuits 25 and the amplifiers 26 are similarly provided corresponding to the array elements. The reference numeral 27 designates a delay period control circuit, and 28 a waveform adder. The waveform adder 28 serves to add up all reception signals obtained simultaneously as the result of delaying in the delay period control circuit 27. The reference numeral 29 designates a peak detector having a gate function for picking up signals in a predetermined range of depth from the surface of the object 3 and a function for storing only a peak value within the range and sending out the peak value. The reference numeral 30 designates an A/D converter for converting the peak value stored in the peak detector 29, into a digital value.

The configuration and operation of the pulser-amplifier switching circuit 24 will be now described with reference to FIG. 5 and FIG. 6 (diagrams (A) through (0)). FIG. 5 is a block diagram of the pulser-amplifier switching circuit, and FIG. 6 (diagrams (A) through (0)) is a timing chart of the pulser-amplifier switching circuit. For simplification of illustration, FIGS. 5 to 6 show the case where the number of array elements to be excited at once is four. As shown in FIG. 5, the pulser-amplifier switching circuit 24 is constituted by a shift register formed by series connection of R-S master-slave flip-flop circuits (hereinafter referred to as merely "flip-flop") $F_1$ to $F_{n+3}$ in the number corresponding to the number of the array elements. In the drawing, $Q_1$ to represent output signals of the flip-flops $F_1$ to $F_{n+3}$. The pulser-amplifier switching circuit 24 operates as follows.

As shown in the diagram (B) of FIG. 6, clear pulses are fed to the CLR terminals of the flip-flops $F_1$ to $F_{n+3}$, so that the levels of all the output signals $Q_1$ to $Q_{n+3}$ become low. Then, as shown in the diagrams (C) to (F) of FIG. 6, preset pulses $PR_1$ to $PR_4$ are fed to the PR terminals of first four flip-flops $F_1$ to $F_4$ In this condition, clock pulses $C_1$, $C_2$, ... as shown in the diagram (A) of FIG. 6A are fed from a clock generator (not shown) to the CK terminals of the flip-flops $F_1$ to $F_{n+3}$, successively.

Then, the levels of the output signals $Q_1$ to $Q_4$ of the flip-flops $F_1$ to $F_4$ each in a preset state become high as shown in the diagrams (G) to (J) of FIG. immediately after the preset pulses $PR_1$ and $PR_4$ are received. These four high-level output signals $Q_1$ to $Q_4$ serve as excitation signals for four array elements of from the first-order element to the fourth-order element. The excitation signals are fed to the four array elements in a first time $E_1$. Then, when the clock pulse $C_1$ is received, the level of the output signal $Q_1$ becomes low as shown in FIG. 6(G) because the level of the S terminal of the flip-flop $F_1$ is low. At the same time, the level of the S terminal of the flip-flop $F_5$ becomes high on the basis of the output signal $Q_4$, so that the level of the output signal $Q_5$ thereof becomes high as shown in the diagram (K) of FIG. 6. Accordingly, excitation signals are fed to four array elements of from the second-order array element to the fifth-order array element in a next time $E_2$. When the next clock pulse $C_3$ is received, the levels of the output signals $Q_3$ to become high in a time $E_3$ in the same manner as described above. Thus, high-level output signals are successively shifted one by one, so that the array elements are successively selected by fours.

In the following, the operation of the pulser-amplifier switching circuit 24 shown in FIG. 4 is described with reference to FIG. 7. FIG. 7 is a simplified block diagram of an array element excitation circuit. Like numerals in each of FIGS. 4 and 7 refer to like parts. For simplification of illustration, a circuit corresponding to one array element $10_1$ is shown in FIG. 7. As described above, the number of the pulsers 23, the number ((n+3) in FIG. 3) of the AND circuits 25 and the number of the amplifiers 26 are, in practice, respectively equal to the number, n, of the array elements. When instructions from the CPU 20 are given to the pulser-amplifier switching circuit 24, the level of the output signal $Q_1$ of the flip-flop $F_1$ becomes high as described above. The output signal $Q_1$ is fed to the AND circuit 25 and then taken out from the AND circuit 25 after a predetermined delay period given by the delay period control circuit 22. On the basis of the output signal, the pulser 23 generates an excitation pulse to excite the array element $10_1$ to thereby emit a supersonic wave. Further, the output signal $Q_1$ is connected also to the amplifier 26. This signal serves as a trigger signal for the amplifier 26, so that the amplifier 26 operates when the level of the output signal $Q_1$ is high but the operation of the amplifier 26 stops and the input signal of the amplifier 26 is not transmitted to the output side thereof when the level is low. The fact that the operation stops means the fact that the input signal of the amplifier 26 is not transmitted to the output side thereof. The reflected supersonic wave is received by the same array element $10_1$ and converted into an electric signal. The electric signal is amplified by the amplifier 26 and delayed for a time determined by the reception delay period control circuit 27 and equal to the time determined by the transmission delay period control circuit 22. Then, the signal is fed to the waveform adder 28. The waveform adder 28 serves to add up (four) reception signals of simultaneously excited array elements to feed an adder signal to the image memory 20b of the signal processor 20 via the peak detector 29 and the A/D converter 30. The aforementioned procedure is repeated n times while array elements are successively shifted by one, so that the adder signals thus successively obtained are stored in the image memory 20b. By the n times procedures, one-line ultrasonic wave scanning in the X-axis direction by use of the array probe 10 is perfected. Then, the CPU 20a drives the motor 7M to move the array probe 10 by a predetermined sampling pitch (YP) in the Y-axis direction. Then, the aforementioned procedure started by application of clear pulses is repeated again to carry out ultrasonic scanning in the X-axis direction by use of respective array elements. As described above, X-axis direction ultrasonic scanning and Y-axis direction sampling pitch movement are repeated to thereby carry out flaw detection in a predetermined range of coordinates (X, Y) in a plane in the object 3. The time required for scanning one line in the X-axis direction is very short because of the electronic scanning, so that the motor in the Y-axis direction can be driven continuously.

Through the aforementioned operation, flaw detection data at intersections determined by the X-axis direction sampling pitch XP (for example, the distance between adjacent array elements) and the Y-axis direction sampling pitch YP are stored in the image memory 20b. The signal processor 20 processes the data stored in the image memory 20b so that the resulting data are displayed on the display unit 21. FIG. 8 shows an example of display in the display unit. In the drawing, the reference numeral 21D designates a display surface of the display unit 21, the reference numeral 3' designates a ultrasonic image of the object 3 displayed on the display surface, and $F_1$ to $f_3$ designate flaw images in the ultrasonic image 3'. The concept "flaw" herein used includes internal separation of an IC package, corrosion of a plating layer of a steel pipe, and gross porosity of a carting. The display surface 21D has a large number of picture elements arranged in the form of a matrix. The picture elements in the display surface 21D are numbered corresponding to the addresses in the image memory 20b, so that the signal processor 20 can carry out display of the data stored in the image memory 20b.

On the other hand, U.S. Pat. No. 4,768,155, a prior art reference, discloses a supersonic flaw detecting system in which a probe of single type, not array type, is mechanically moved both in the X-axis direction and in the Y-axis direction for the purpose of scanning.

Because this ultrasonic flaw detecting system conducts mechanical scanning in the X-axis direction as well as in the Y-axis direction, the time required for obtaining one scene is of the order of tens of seconds.

The first prior art type supersonic flaw detecting system as described above with reference to FIGS. 1 to 8 conducts supersonic flaw detection in an X-Y plane (A scope) in a predetermined depth from the surface of the object 3 to obtain a ultrasonic image in the plane, so that existence of flaws can be found.

To perform more excellent production control and quality control, detailed data of flaw such as position of a flaw depth, a flaw shape and the like are required. To obtain the information, both an A-scope image (waveform) and a B-scope image (vertical sectional image) in the position of a flaw are required. The second prior art type ultrasonic flaw detecting system is configured so that a C-scope image (horizontal sectional image) is displayed and then an A-scope image can be obtained in a desired position of the C-scope image. However, the system is so slow that the time of from the order of tens of seconds to the order of minutes is required for obtaining the C-scope image, because the scanning both in the X-direction and in the Y-direction is mechanical. On the contrary, the first prior art type system is so speedy that the time required for obtaining the C-scope image is about one second or of the order of seconds, but the system is not suitable for detailed inspection though the detailed inspection is necessary.

SUMMARY OF THE INVENTION

An object of the present invention is to overcome the aforementioned problems of the prior art type ultrasonic flaw detecting system. In other words, an object of the present invention is to provide a ultrasonic flaw detecting system in which quick access to a position on a desired plane where an operator wants to know detailed flaw information in an inspection object displayed on an investigation display screen is allowed by use of cursor means in order to detect more detailed flaw information (such as a flaw type, a flaw position, a flaw size, a flaw shape, and the like) in the object and in which A-scope image and B-scope image at the position in the desired plane can be quickly observed at once.

To attain the foregoing object, according to an aspect of the present invention, the ultrasonic flaw detecting system comprises: an array probe constituted by a large number of array elements arranged in a direction of a first axis for serving transmission and reception of ultrasonic waves; switching means for switching the array elements so as to successively select a predetermined number of ones of the array elements on the basis of a clock signal; moving means for moving the array probe in a direction of a second axis orthogonal to the first axis; delay control means provided both in the transmission side and in the reception side for the double purpose of converging ultrasonic waves at a predetermined point and receiving reflection waves from the point; a display portion for displaying a ultrasonic image in a plane formed by the first and second axes on the basis of signals received by the array elements; cursor display means for displaying a cursor in the display portion; computing means for computing the amount of movement of the cursor; clock signal output control means for generating the clock signal having a number of pulses corresponding to the amount of movement of the cursor in the first axial direction; driving means for driving the moving means corresponding to the amount of movement of the cursor in the second axial direction; and a second display portion for displaying a ultrasonic image in a direction of a third axis orthogonal to the first and second axes, so that the system is capable of simultaneously conducting plane-image display (C-scope display) and waveform display (A-scope display).

According to another aspect of the present invention, the ultrasonic flaw detecting system comprises: an array probe constituted by a large number of array elements arranged both in a direction of a first axis and in a direction of a second axis orthogonal thereto for serving transmission and reception of ultrasonic waves; switching means for switching the array elements so as to successively select a predetermined number of ones of the array elements on the basis of a clock signal; delay control mean provided both in the transmission side and in the reception side for the double purpose of converging ultrasonic wave at a predetermined point and receiving reflection waves from the point; a display portion for displaying a ultrasonic image in a plane formed by the first and second axes on the basis of signals received by the array elements; cursor display means for displaying a cursor in the display portion; computing means for computing the amounts of movement of the cursor in the first and second axial directions; clock signal output control means for generating the clock signal having a number of pulses corresponding to the amount of movement of the cursor in the first axial direction and for generating the clock signal having a number of pulses corresponding to the amount of movement of the cursor in the second axial direction; and a second display portion for displaying a ultrasonic image in a direction of a third axis orthogonal to the first and second axes, so that the system is capable of simultaneously conducting plane-image display (C-scope display) and waveform display (A-scope display).

When a plane ultrasonic image is obtained in the display portion and then more detailed analysis in a desired position of the ultrasonic image is required, a cursor can be displayed in the display portion and can be quickly moved to the desired position. With the movement of the cursor, the distances of the movement in the first and second-axis directions which form the plane are computed by the computing means. In the case where the array probe is constituted by array elements arranged in the first-axis direction, a number of clock pulses corresponding to the distance of the first-axis direction movement of the cursor are generated and, at the same time, the array probe is moved in the second axis direction by a distance corresponding to the distance of the second-axis direction movement of the cursor. In the case where the array probe is constituted by array elements arranged in the form of a matrix in the first and second-axis directions, a number of clock pulses corresponding to the distance of the first axis direction movement of the cursor and a number of clock pulses corresponding to the distance of the second axis direction movement of the cursor are given to the first and second-axis directions of the array elements. Accordingly, in any case, ultrasonic waves converged into the desired position in the plane, of the object corresponding to the position of the cursor is emitted. Reflected wave of the ultrasonic wave is received and displayed in the other display portion having a time axis. Accordingly, a ultrasonic image in a direction of an axis orthogonal to the first and second axes can be obtained in the desired position of the object corresponding to the position of the cursor, so that more detailed analysis can be made on the basis of the supersonic image.

In short, as described above, the first prior art type system has a disadvantage in that neither A-scope image nor B-scope image can be observed, and the second prior art type system has a time restriction in that a long time of the order of tens of seconds is required for forming a C-scope screen. According to the present invention, not only the time required for forming a C-scope screen is no more than about 1 second, but also both the A-scope image and B-scope image can be displayed to thereby attain more detailed flaw detection quickly.

BRIEF DESCRIPTION OF THE DRAWINGS

The prior art type supersonic flaw detecting system is shown in FIGS. 1 to 8, in which.

Figure 9:
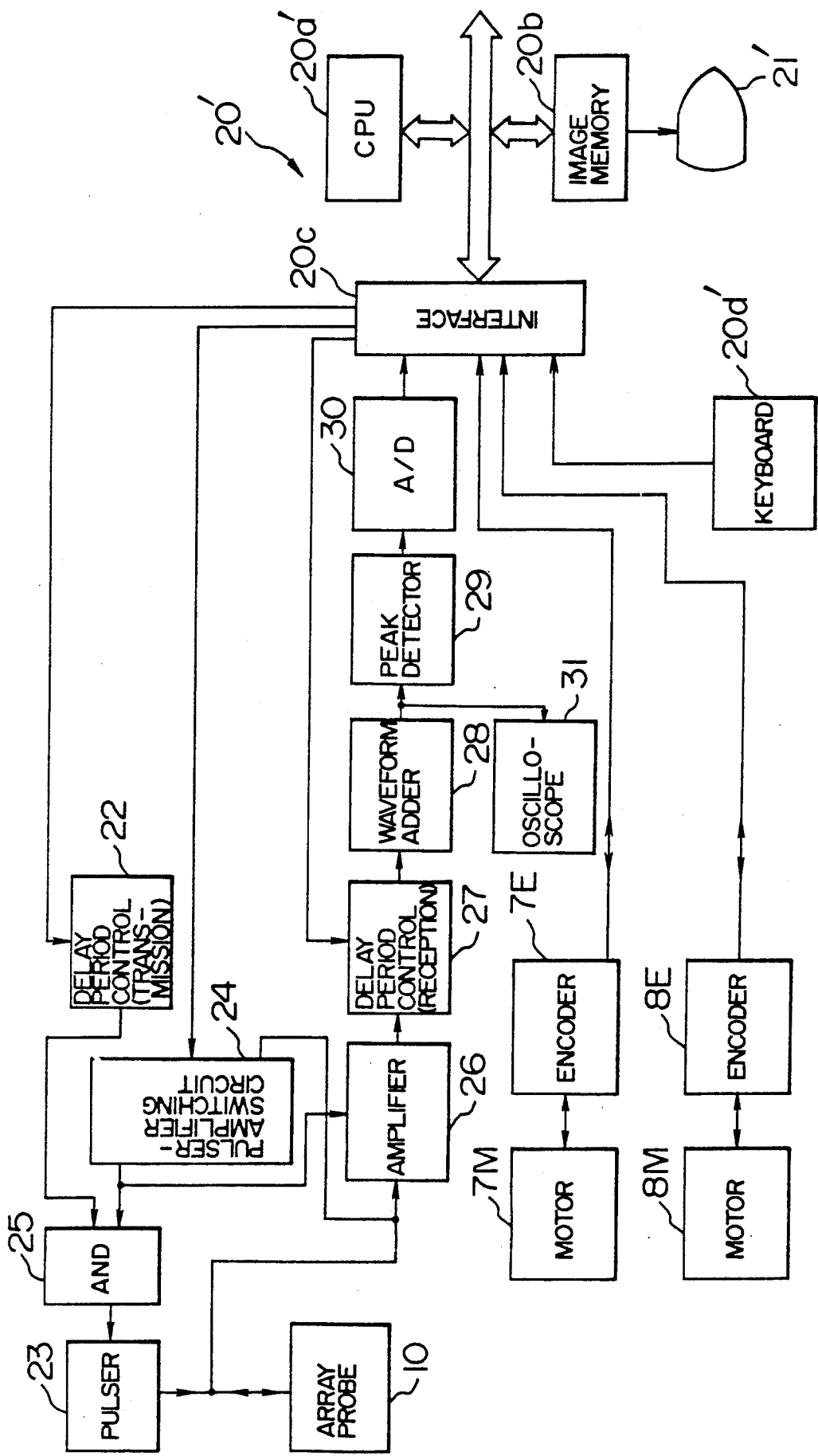
Figure 11A:
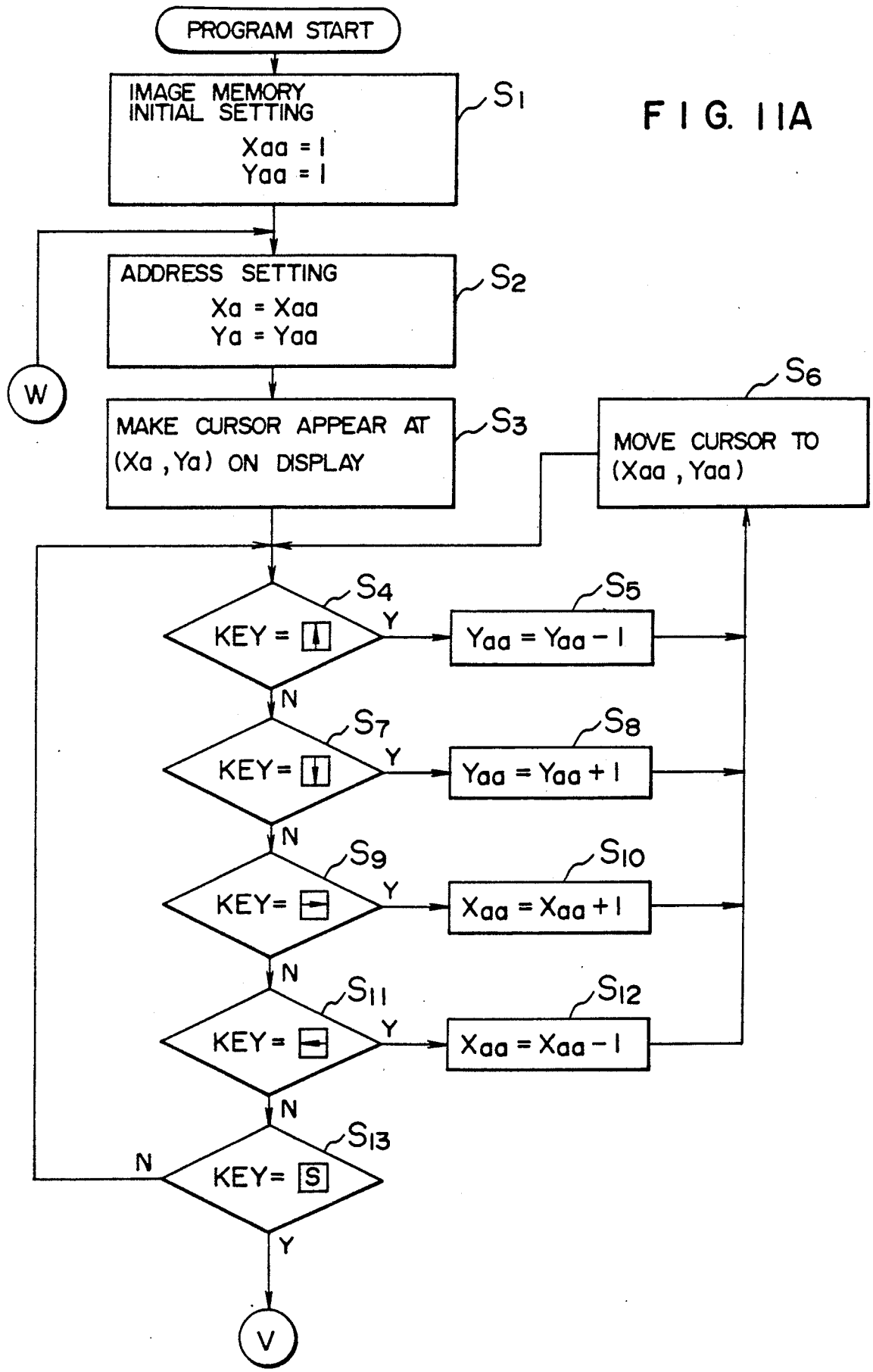
Figure 11B:
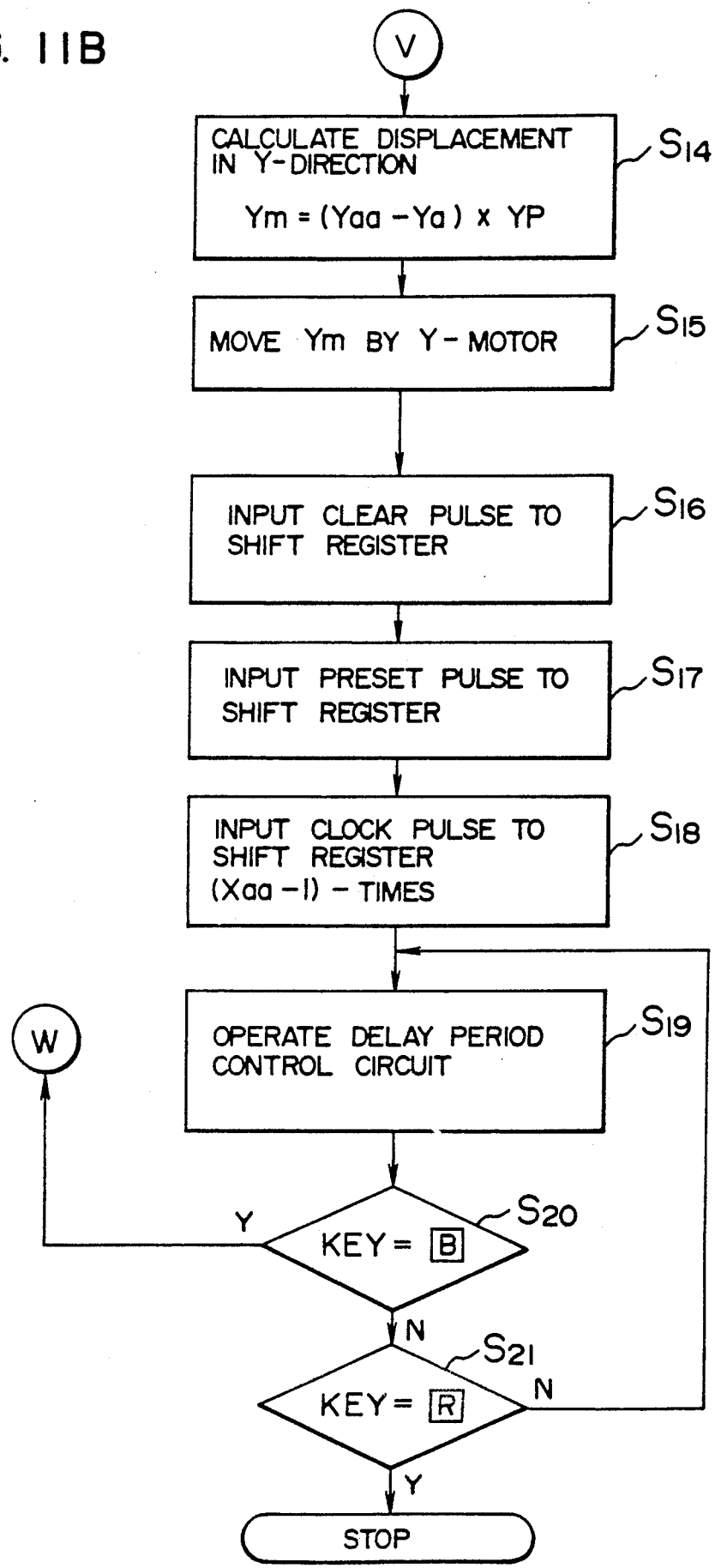
Figure 12:
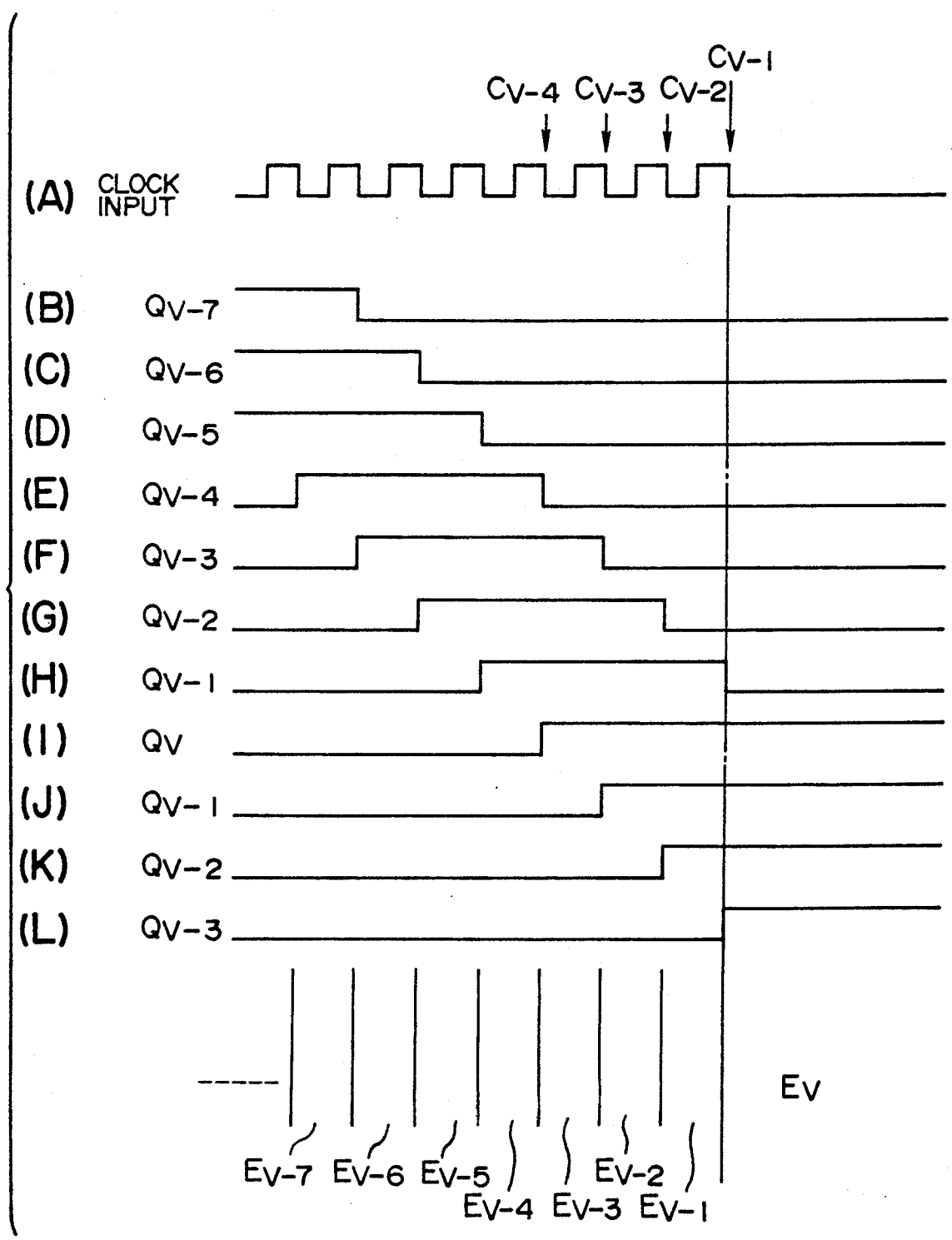

An embodiment of the present invention is shown in FIGS. 9 to 12, in which:

FIG. 9 is an electric circuit block diagram of a ultrasonic flaw detecting system as an embodiment of the present invention;

FIG. 10 is a front view showing the display plane of the display unit depicted in FIG. 9;

FIGS. 11A and 11B are flow charts for explaining the operation of the system depicted in FIG. 9; and FIG. 12 (including diagrams (A) to (L)) is a timing chart for explaining the operation of the system depicted in FIG. 9.

Figure 4:
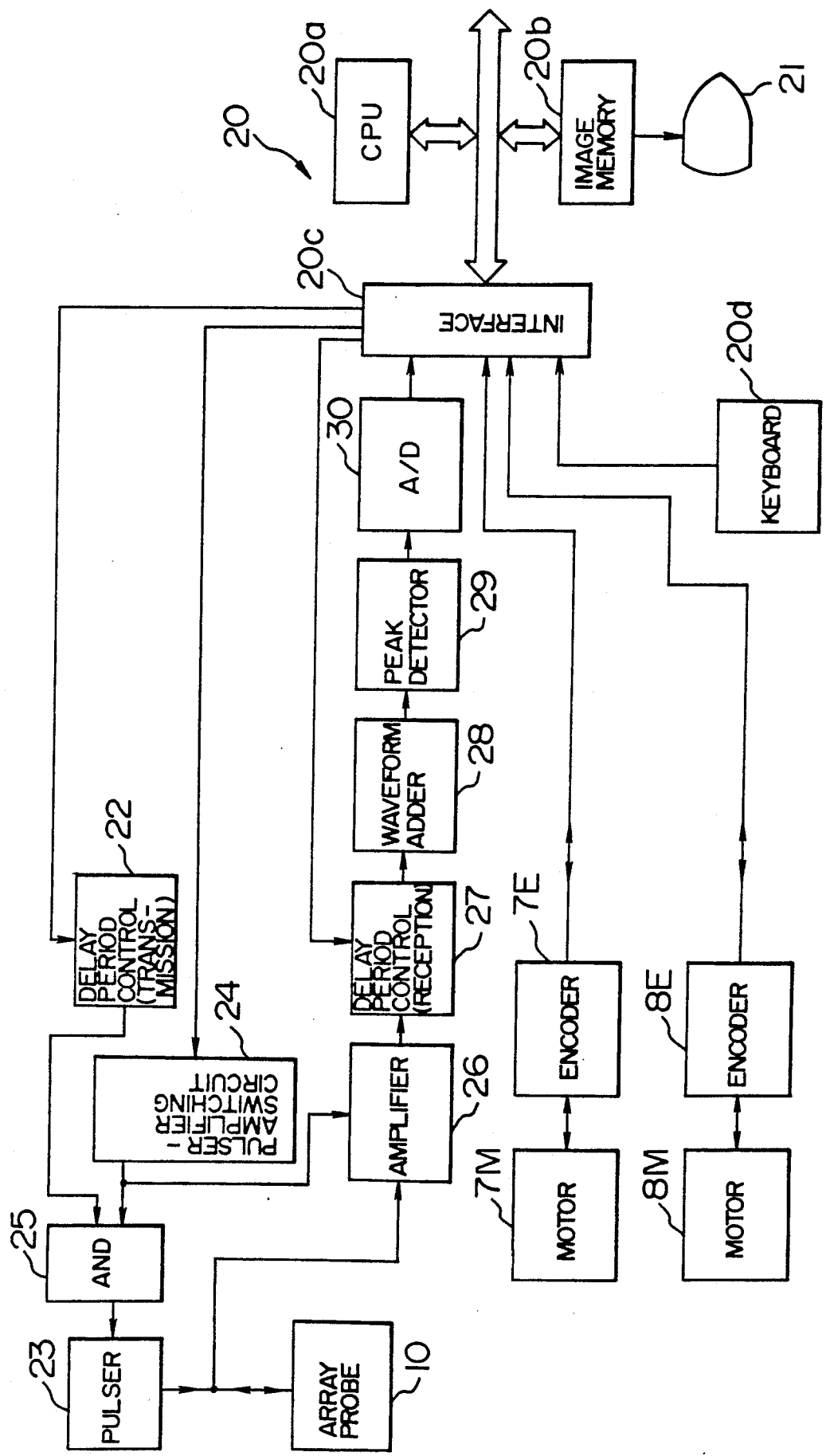
FIG. 4 is a block diagram showing an example of electric circuit configuration of the prior art type ultrasonic flaw detecting system.
Figure 13:
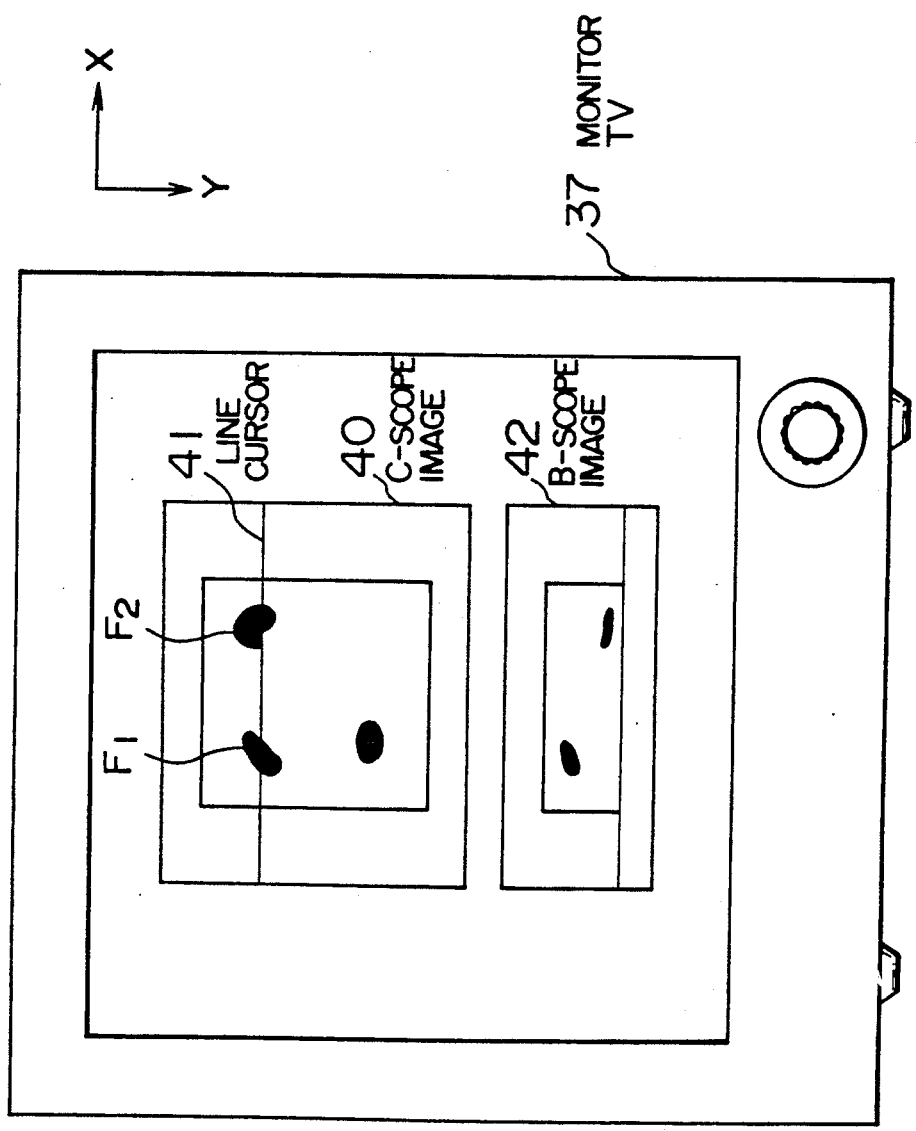
Figure 14:
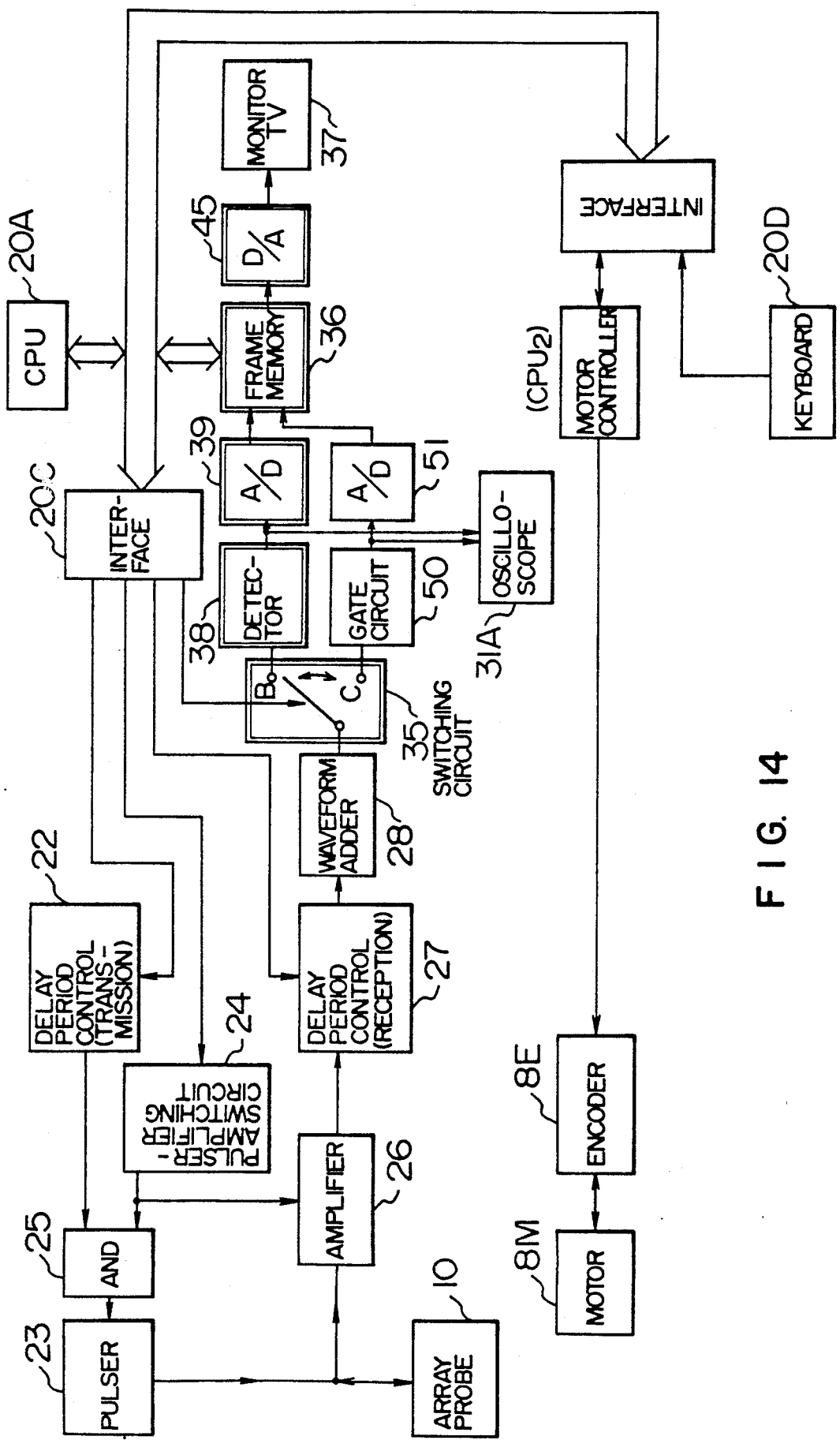
Figure 15A:
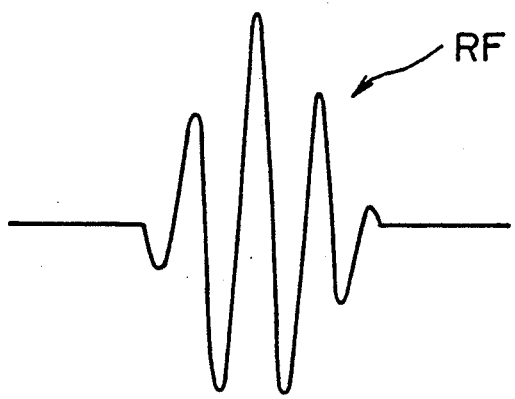
Figure 15B:
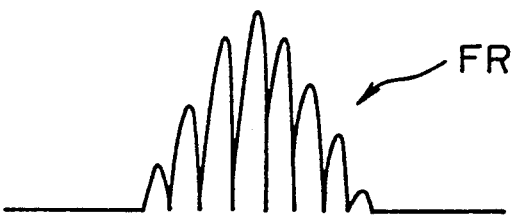
Figure 15C:
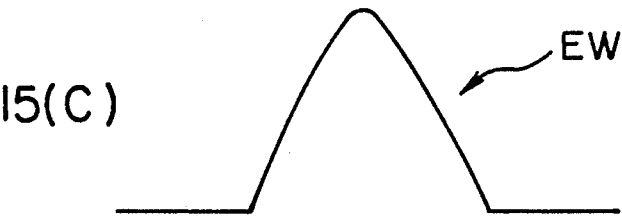
Figure 15D:
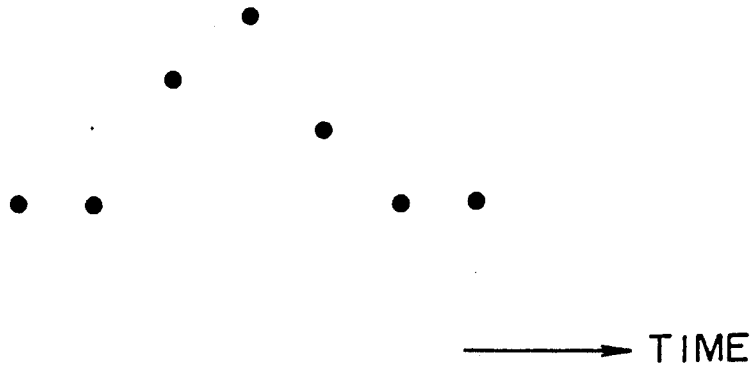
Figure 16A:
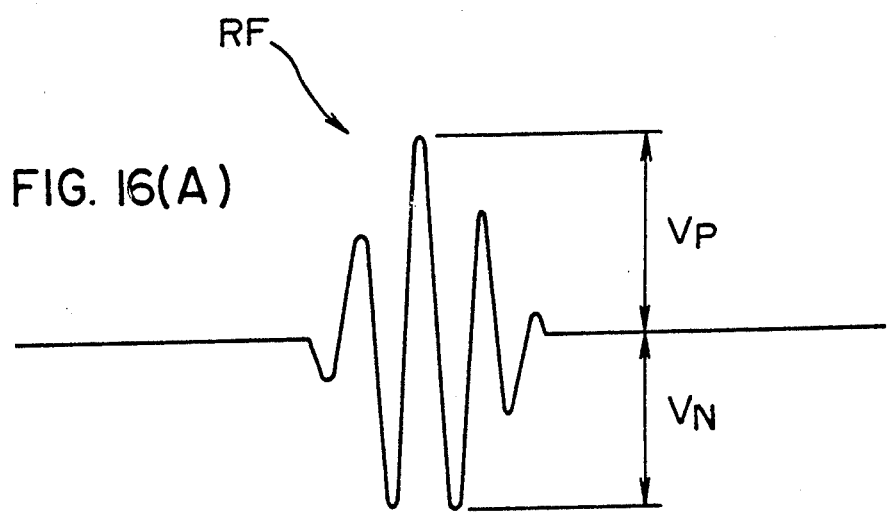
Figure 16B:
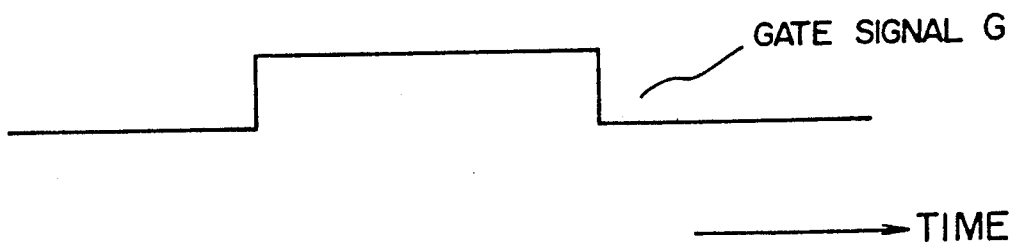

Another embodiment of the invention is shown in FIGS. 13 to 16, in which:

FIG. 13 is a front view showing the display plane of a TV monitor;

FIG. 14 is an electric circuit block diagram similar to FIG. 4;

FIG. 15 shows signal-processed waveforms (A) to (D) for forming a sectional-image (B-scope image) of an object to be inspected; and FIG. 16 shows signal-processed waveforms (A) and (B) for forming a plane image (C-scope image) of the object.

DESCRIPTION OF THE PREFERRED EMBODIMENTS

The present invention will be described hereunder with reference to the preferred embodiments shown in the drawings.

FIG. 9 is a block diagram of a control circuit in an embodiment of the ultrasonic flaw detecting system according to the present invention. In FIG. 9, items the same as or equivalent to those in FIG. 4 are referenced correspondingly. In FIG. 9, the reference numeral 20a' designates a CPU similar to the CPU 20a but different from the latter in processing contents. The reference numeral 20d' designates a keyboard similar to the keyboard 20d but different from the latter in that the keyboard 20d' includes cursor operation keys. The cursor operation keys include seven keys, that is, a cursor up key ( ↑ ), a cursor down key ( ↓ ), a cursor left key (←), a cursor right key (→), a cursor stop key (S), a key (B) used when the cursor is moved from the current position, and a cursor function program stop key (R). The reference numeral 20' designates a signal processor constituted by a CPU 20a', an image memory 20b, an interface 20c and a keyboard 20d°. The reference numeral 21' designates a display unit similar to the display unit 21. The display unit 21' will be described later. The reference numeral 31 designates an oscilloscope for displaying an output signal of the waveform adder 28. The arrangement of parts in FIG. 9 is the same as that of parts in FIG. 4, except the signal processor 20', the display unit 21' and the oscilloscope 31.

Figure 8:
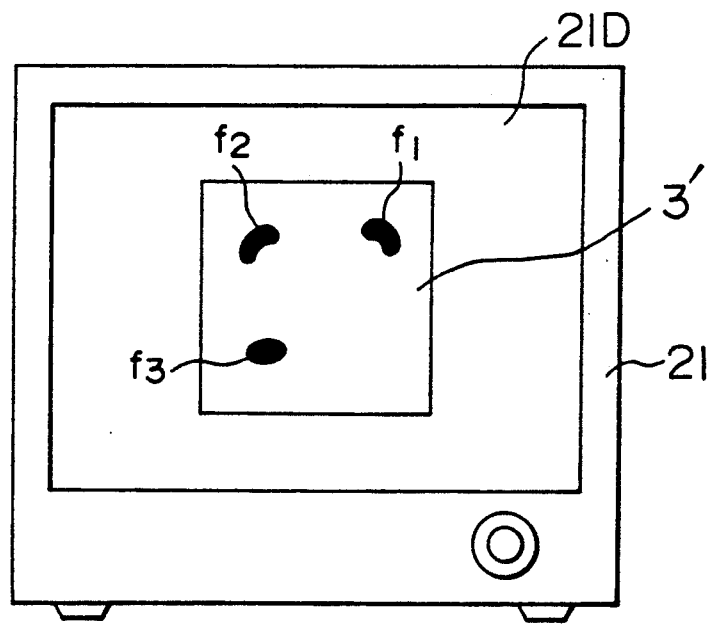
FIG. 8 is a front view showing the display plane of the display unit depicted in FIG. 4.

FIG. 10 is a view showing the display surface of the display unit shown in FIG. 9. In FIG. 10, items the same as or equivalent to those in FIG. 8 are referenced correspondingly. In FIG. 10, the reference numeral 21' designates a display unit, and 21D' a display surface thereof. In FIG. 10, C represents a cursor displayed on the display surface 21D'. The display unit 21' is different from the display unit 21 in that the display unit 21' has means for displaying the cursor C. In the case where cursor display control can be replaced by the display unit 21. The cursor C is displayed in a ultrasonic scanning start point $(X_1, Y_1)$. The cursor C can be moved vertically and horizontally on the basis of cursor operation keys (not shown) in the keyboard 20d'.

Figure 1:
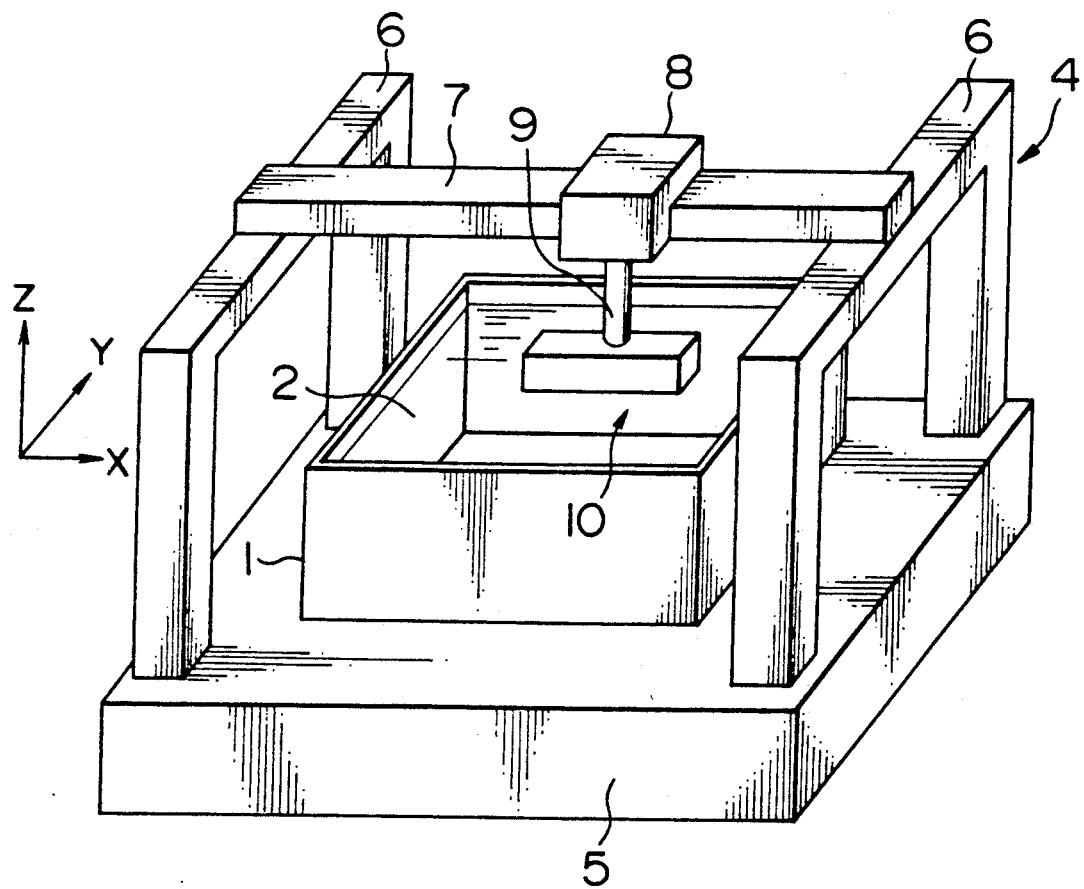
FIG. 1 is a perspective view of a scanner portion of the ultrasonic flaw detecting system.
Figure 2A:
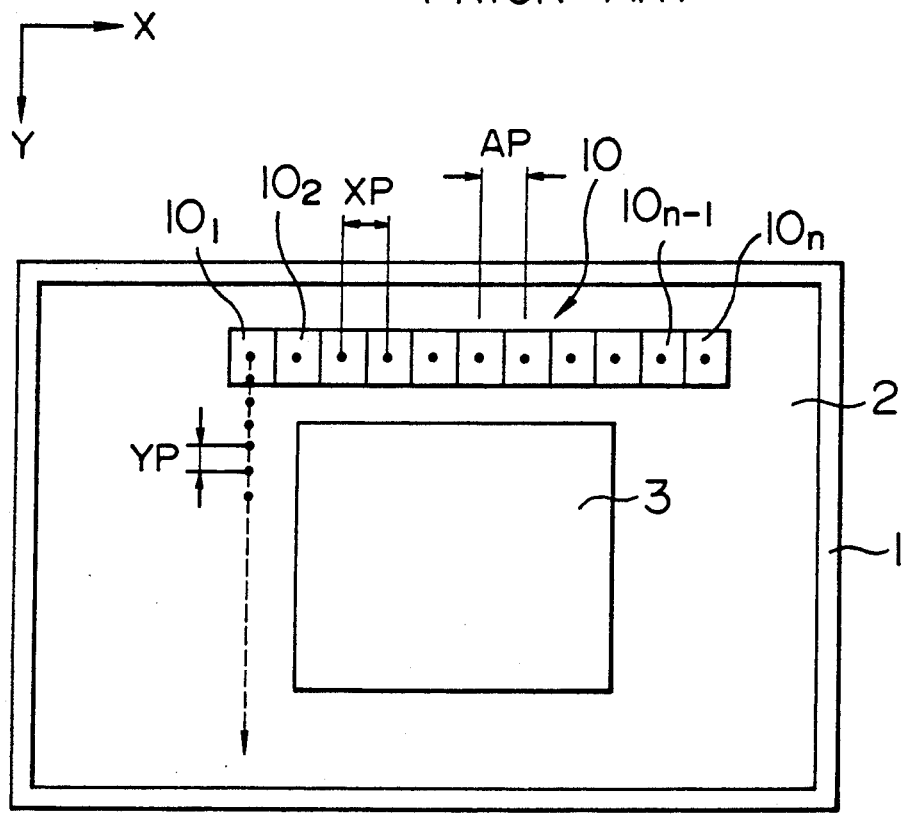
FIGS. 2A and 2B are a plan view and a side view of an array probe.
Figure 2B:
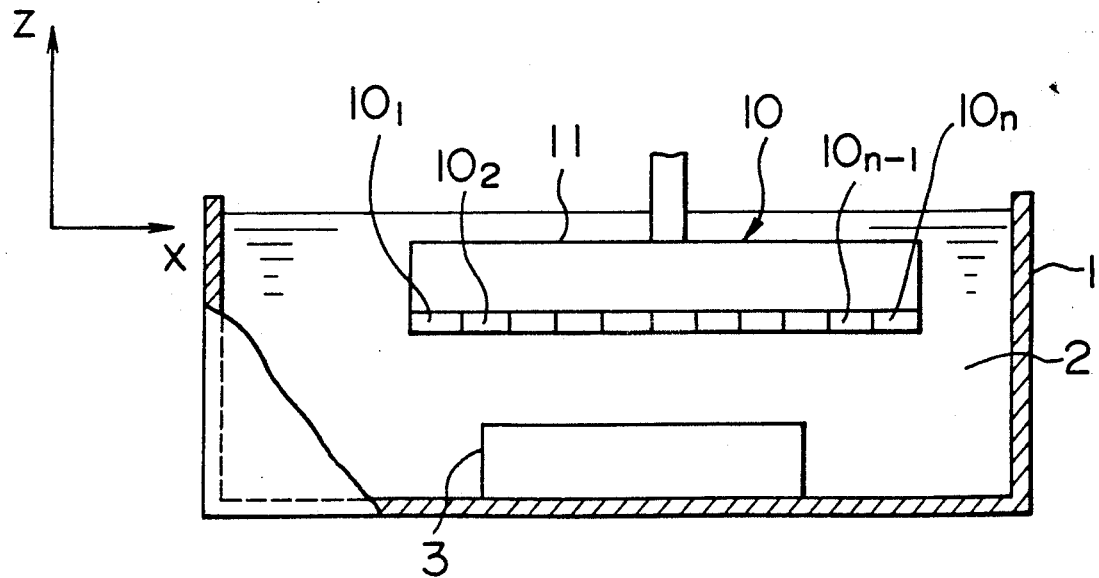
Figure 3B:
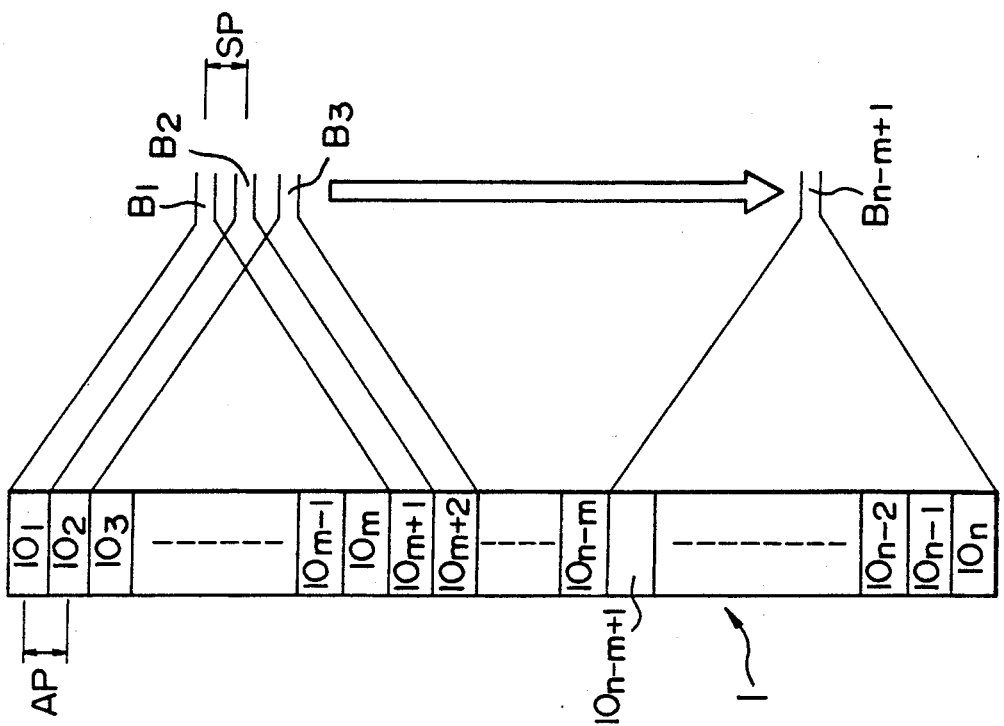
FIGS. 3A and 3B are views for explaining the focusing function of the array probe.
Figure 3A:
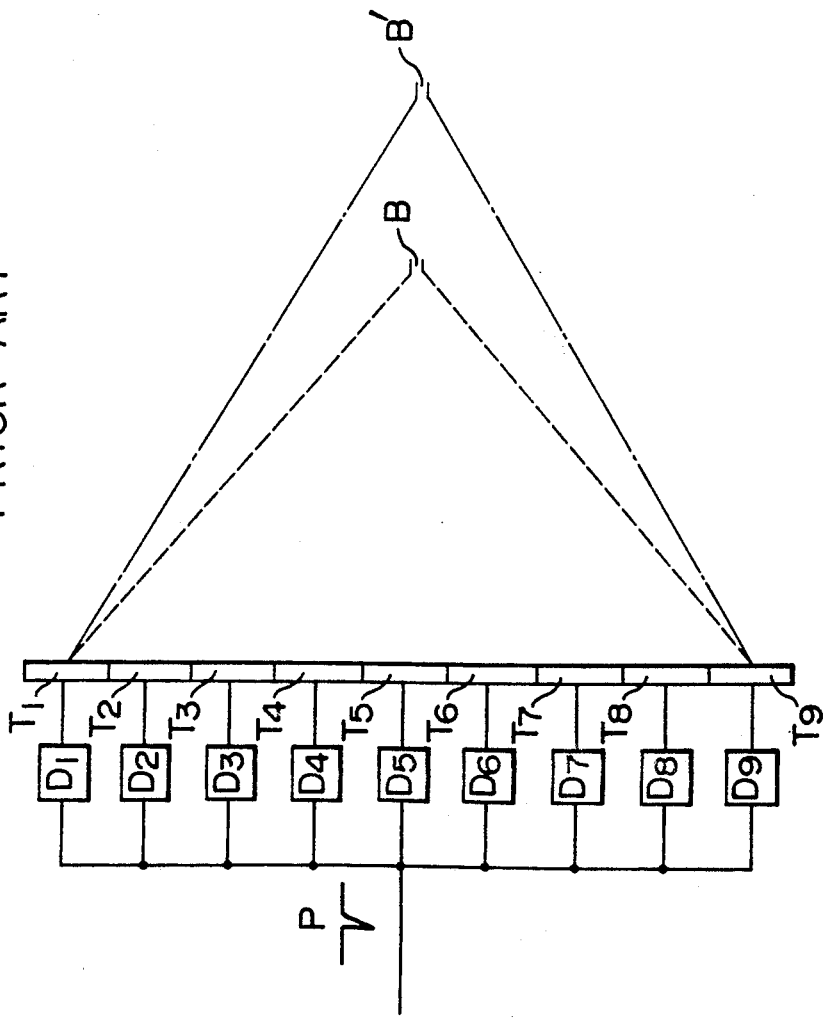

In the following, the operation of this embodiment is described with reference to the flow charts of FIGS. 11A and 11B and the timing charts of FIG. 12 including the diagrams (A) to (L). First, the CPU 20a' initializes the image memory 20b (the step $S_1$ in FIG. 11A). In other words, addresses $X_{aa}$ and $Y_{aa}$ corresponding to the supersonic flaw detection start point in the X-axis direction address $X_a$ and the Y-axis direction address $Y_a$ in the image memory 20b are initialized. In this case, $X_{aa}=1$ and $Y_{11}=1$. Then, address setting is carried out so that addresses Xa and Ya in the movement start time are $X_{aa}$ and $Y_{aa}$, respectively (the step $S_2$). Then, a cursor C is displayed in a position $(X_a, Y_a)$ of the display surface 21D' corresponding to the addresses $X_a$ and $Y_a$ (the step $S_3$). In this case, $X_{aa}=12$ and $Y_{aa}=1$, so that the cursor C is displayed in the ultrasonic flaw detection start position $(X_1, Y_1)$ as shown in FIG. 10. Thereafter, the cursor C is moved to a desired position, for example, position $(X_v, Y_w)$ in FIG. 2, by the steps $S_4$ to $S_{13}$. The movement is made by shifting the cursor C by one picture element (one address) according to the movement instruction direction of the operation key, judging which of four cursor operation keys instructing to move the cursor up, down, left and right is operated in the keyboard 20d°'. In the case of FIG. 10, the cursor C is moved by (V−1) in the X-axis direction and by (W−1) in the Y-axis direction. In the step $S_{13}$, a judgment is made as to whether the cursor stop key S is operated or not, when the position of the cursor C is decided, the procedure is shifted to the step $S_{14}$ in FIG. 11B.

In the step $S_{14}$, how much the array probe 10 must be moved in the Y-axis direction is computed.

When the distance of movement is represented b $Y_m$, $Y_m$ sampling pitch YP by a value obtained by subtracting the movement start-time address $Y_a$ from the current Y-axis direction address $Y_{aa}$. In the case of FIG. 10, $Y_{aa}=W$ and $Y_a=1$. Accordingly, the distance $Y_m$ of the Y-axis direction movement of the cursor C is represented by the equation $Y_m=(W-1)\cdot YP$. The CPU 20a' drives the motor 7M to move the array probe 10 by $Y_m$ in the Y-axis direction (the step $S_{15}$). In short, the aforementioned procedure is a procedure for moving a ultrasonic beam to the Y-axis direction position $Y_w$.

Figure 5:
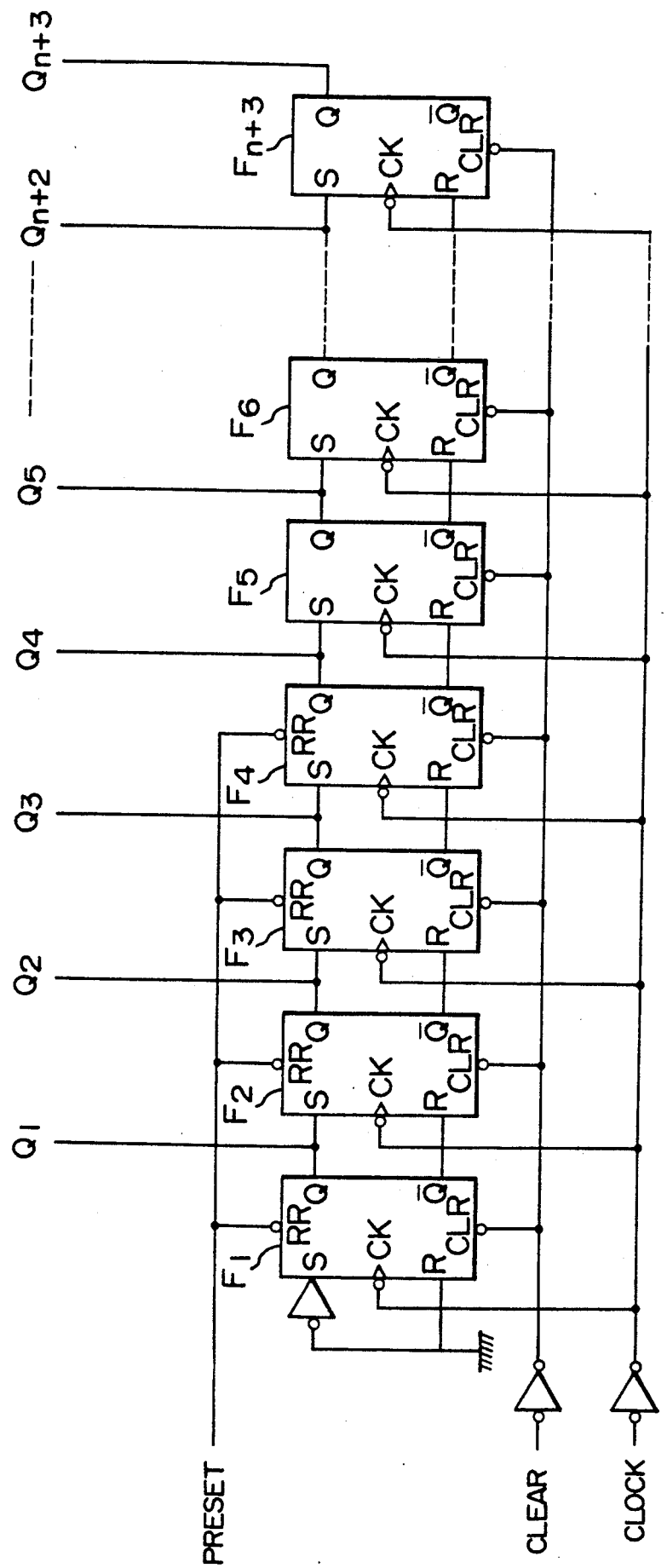
FIG. 5 is a block diagram showing in detail the pulser-amplifier switching circuit depicted in FIG. 4.
Figure 6:
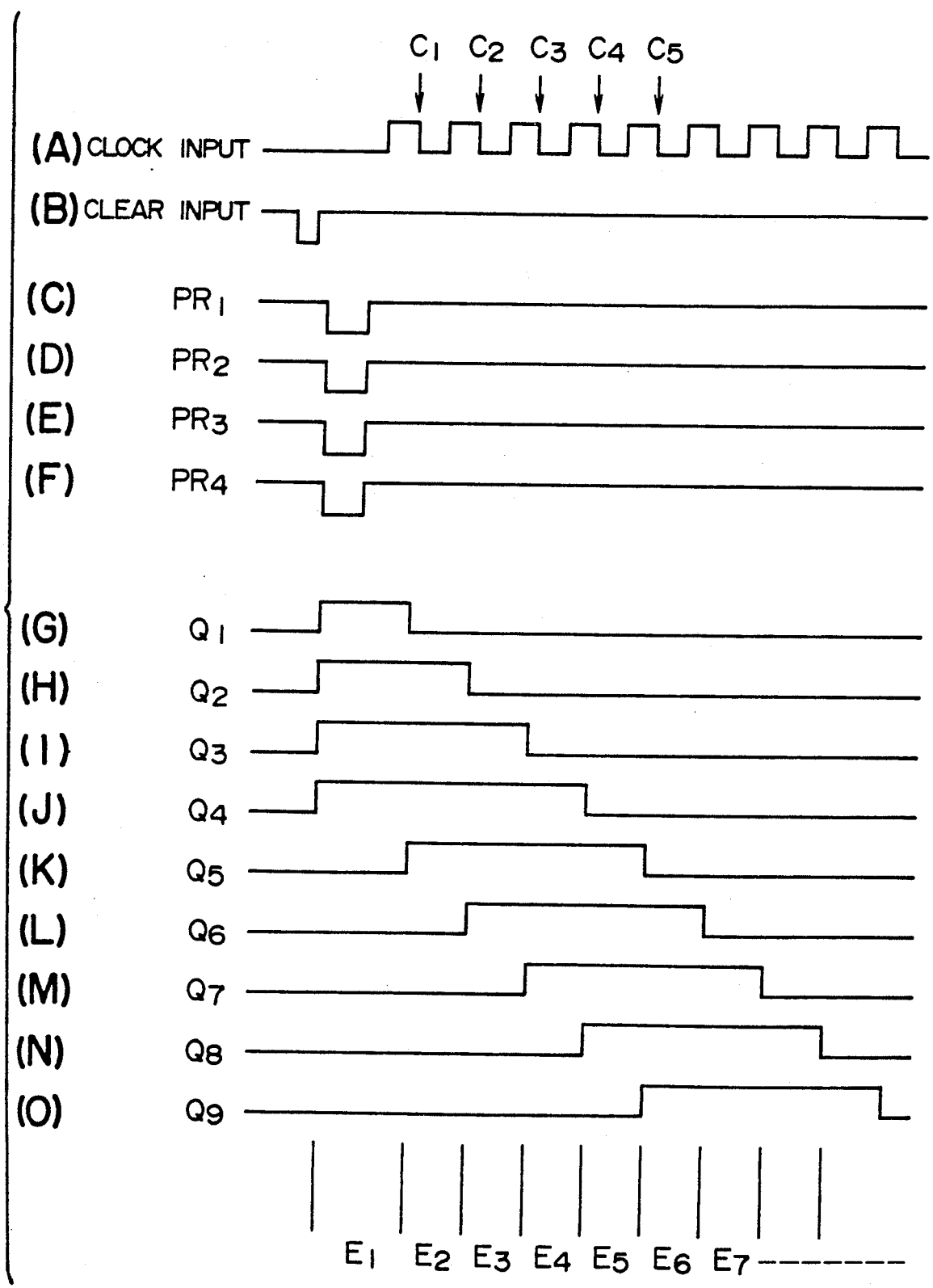
FIG. 6 (including diagrams (A) to (0)) is a timing chart for explaining the operation of the pulser-amplifier switching circuit.
Figure 7:
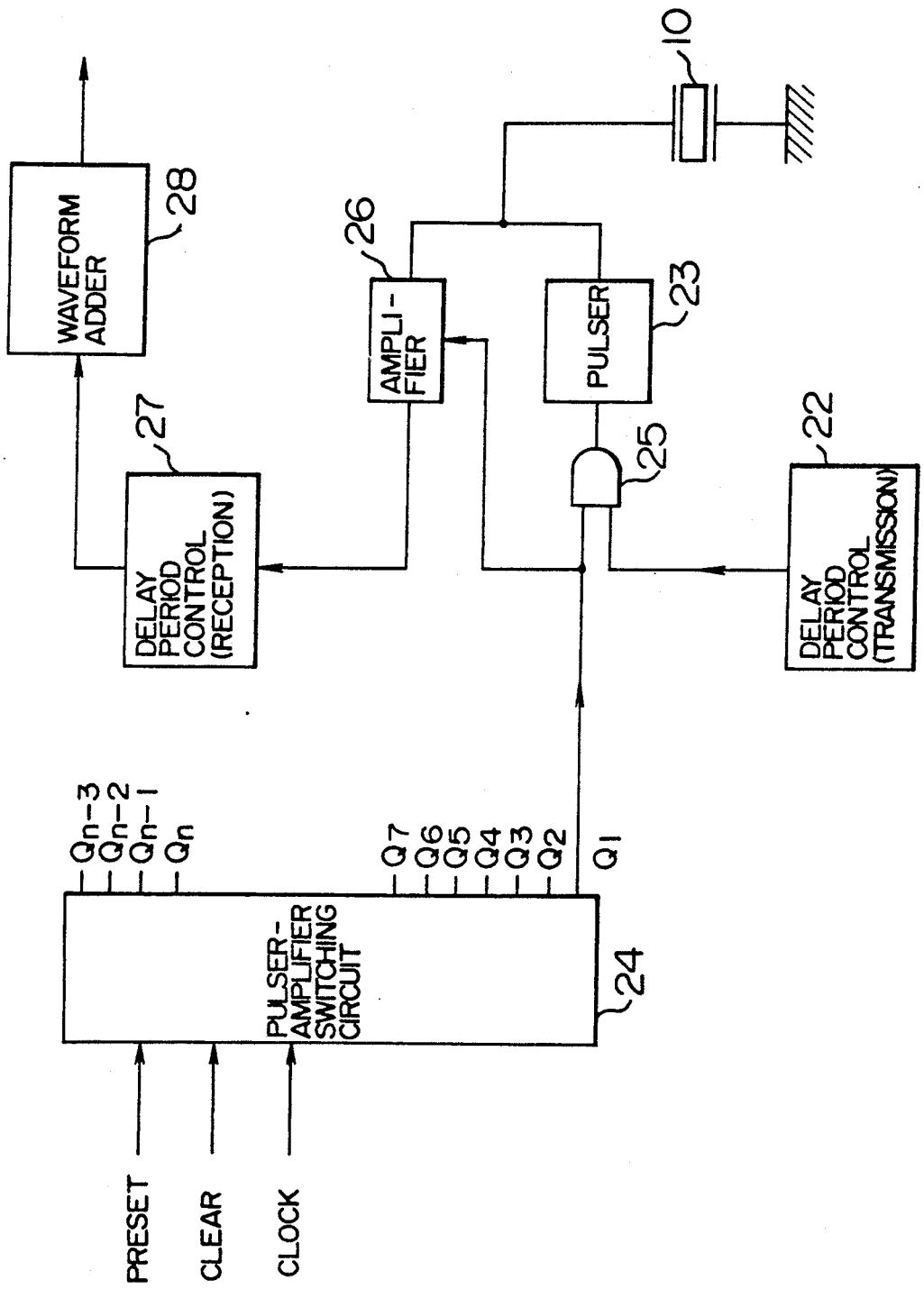
FIG. 7 is a block diagram showing in detail a part of the circuit depicted in FIG. 4.

In the following, the procedure for moving a ultrasonic beam to the X-axis direction position $X_v$ is described As described above, the ultrasonic beam can be moved in the X-axis direction by one array element pitch (sampling pitch XP) whenever one clock pulse is given to the shift register (composed of flip-flops) forming the pulser-amplifier switching circuit 24. Now, clear pulses are given to the shift register as described above (the step $S_{16}$) and then preset pulses are given to simultaneously excited array elements (the ste $S_{16}$). When, in this condition, clock pulses are given, the ultrasonic beam is successively shifted in the X-axis direction for every clock pulse. The clock pulse is given at $(X_{aa}-1)$ times (the ste $S_{18}$). In the following, the output state of the shift register and the X-axis direction position of the ultrasonic beam when the clock pulse is given at $(X_{aa}-1)$ times are explained by reference to Table. In this case, it is assumed that the number of simultaneously excited array elements is four as shown in FIG. 5 and the position of X-axis direction movement of the cursor is position $X_y$ as shown in FIG. 10.

| Clock pulse | Position in X-direction (pixel number) | Shift register output to become high level |
|---|---|---|
| — | $X_1$ | $Q_1 \sim Q_4$ |
| $C_1$ | $X_2$ | $Q_2 \sim Q_5$ |
| $C_2$ | $X_3$ | $Q_3 \sim Q_6$ |
| $C_3$ | $X_4$ | $Q_4 \sim Q_7$ |
| $C_4$ | $X_5$ | $Q_5 \sim Q_8$ |
| . | . | . |
| . | . | . |
| $C_{v-1}$ | $X_v$ | $Q_v \sim Q_{v+3}$ |
| . | . | . |
| . | . | . |
| $C_{n-2}$ | $X_{n-1}$ | $Q_{n-1} \sim Q_{n+2}$ |
| $C_{n-1}$ | $X_n$ | $Q_n \sim Q_{n+3}$ |

As shown in the above Table, before the first order clock pulse $C_1$ is given, the levels of the output signals $Q_1$ to $Q_4$ become high to excite the first four array elements. In this case, the X-direction convergent position of the ultrasonic beam is made to coincide with the position $X_1$. Then, after the first-order clock pulse $C_1$ is given, the levels of the output signals $Q_2$ to $Q_5$ of the shift register become high, so that simultaneously excited array elements are shifted by one in the X-axis direction and, accordingly, the convergent position of the supersonic beam is shifted by one array element pitch, that is, one sampling pitch XP. Accordingly, the convergent position of the ultrasonic beam becomes the position $X_2$. This operation is repeated. When the (V-1)th-order clock pulse $C_{v-1}$ is given, the levels of the output signals $Q_v$ to $Q_{v+3}$ become high and, accordingly, the convergent position of the ultrasonic beam becomes the position $X_v$.

This is explained by reference to the timing chart of FIG. 12 including the diagrams (A) to (L). When the clock pulse $C_{v-1}$ is given, the high-level output signals of the shift register are the output signals $Q_v$ to $Q_{v+3}$. When generation of the clock pulse stops thereafter, the aforementioned state is kept during a period represented by time $E_v$. Accordingly, a state to radiate the supersonic beam in the position $X_v$ at time $E_v$ is adjusted. When the delay period control circuit 22 is operated from this state (the ste $S_{19}$), predetermined delay periods are given to the output signals $Q_v$ to $Q_{v+3}$ in the AND circuit 25 to move the pulser 23. Because the array probe 10 has been moved to the Y-axis direction position $Y_w$, the supersonic beam is radiated to the position ($X_v$, $Y_w$). The reflected wave of the ultrasonic beam is received by excited array elements and then sent out from the waveform adder 28 as described above. The oscilloscope 31 is operated on the basis of the output signal of the waveform adder 28 to display the waveform of the signal. In this case, the waveform (A-scope image) is a Z-axis direction ultrasonic flaw detection waveform in the ($X_v$, $Y_w$), by which more detailed flaw detection in the position is carried out.

Then, the CPU $20a'$ judges the state of the cursor operation key B in the keyboard $20d'$ (the step $S_{20}$). When the cursor operation key B is judged to be inoperative, the state of the cursor operation key R is judged (the step $S_{21}$). When the cursor operation key R is judged to be inoperative, the procedure is returned to the step $S_{19}$ so that a ultrasonic beam is repeatedly radiated to the position ($X_v$, $Y_w$) and then the reflected waveform is displayed on the oscilloscope 31. When, in the step $S_{20}$, the cursor operation key B is judged to L 25 be operative, the procedure is returned to the step $S_2$ so that the movement of the cursor C is carried out again. In this case, the addresses $X_{aa}$ and $Y_{aa}$ correspond to the movement start position When, in the step $S_{21}$, the cursor is judged to be operative, the operation of emitting ultrasonic waves to the position stops.

As described above, in this embodiment, a cursor is displayed and moved to a desired position of the ultrasonic image obtained by supersonic scanning of a plane of the object by use of a probe array and is moved to a desired position of the ultrasonic image, so that a ultrasonic wave is emitted to a position of the object corresponding to the position and then the reflected signal is observed by the oscilloscope. Accordingly, not only ultrasonic flaw detection on a plane of the object can be conducted but also ultrasonic flaw detection in the depth in the desired position of the object can be conducted. Consequently, more detailed analysis of a flaw portion can be made.

Although the aforementioned embodiment has shown the case where the probe array is mechanically moved in the Y-axis direction, it is apparent that the invention can be applied to the case where the probe has also the probe array in the Y-axis direction, that is, the probe has array elements arranged in the form, of a matrix. Further, the focal position of the ultrasonic beam in the cursor position is constant but when more detailed information in the direction of depth is required, the focal depth can be changed by changing the delay period variously.

An embodiment capable of displaying a plane image (C-scope) and a sectional image (B-scope) at once will be described with reference to FIGS. 13 to 16, in which the same or similar part as in FIG. 9 is referenced correspondingly.

First, a plane image (C-scope image) 40 is displayed on a monitor TV 37 as a display unit in the same manner as in the prior art. Then, a line cursor 41 is presented in parallel to the X-axis direction and moved in the Y-direction by operation of the keyboard 20D.

If observation of a detailed sectional image (B-scope image) 42 in a portion (shown by the line cursor 41) crossing two flaws $F_1$ and $F_2$ as shown in FIG. 13 is required, the B-scope image 42 in the line cursor position can be observed under the plane image (C-scope image) 41 as shown in FIG. 13 by pushing keyboard input key such as return key "RET" while setting the line cursor 41 in the shown position.

At this time, in the Y-direction, the array probe 10 is mechanically moved to the position of the line cursor 41 by the motor. In the X-direction, electronic scanning (in this case, linear scanning) as described above is carried out for B-scope display.

A block diagram of the system in this embodiment is shown in FIG. 14. Double-framed blocks are newly provided. A switching circuit 35 following the waveform adder 28 serves to switch between B-scope display and C-scope display. For example, the switching circuit 35 serves to switch electronically alternately therebetween in a time of the order of msec. When an upper contact of the switching circuit is closed, B-scope display is selected. When a lower contact of the switching circuit is closed, on the contrary, C-scope display is selected.

When the switching circuit 35 is in a state of B-scope display, the output signal thereof passes through a detector circuit 38. The waveform of the input signal of the detector circuit 38 is Rf waveform Rf as shown in the diagram (A) of FIG. 15. The signal is full-wave rectified by the detector circuit 38 to obtain a full-wave rectified waveform FR as shown in the diagram (B) of FIG. 15 and then obtain an envelope waveform EW as shown in the diagram (C) of FIG. 15. In a next-stage A/D converter 39, the output waveform (in the diagram (C) of FIG. 15) of the detector circuit is digitized at a predetermined sampling interval as shown in the view (D) of FIG. 15. If the sampling interval in the A/D conversion is sufficiently small, sampling may be applied to the Rf waveform in the diagram (A) of FIG. 15. However, the A/D conversion is, in practice, not speedy enough to trace the up and down movement of the Rf waveform. Accordingly, the frequency of the waveform is reduced by the detector circuit.

The next subject is how to feed, as a B-scope image 42, the A/D converted data to the monitor TV 37. A method which has been developed and has been put into practical use for ultrasonic diagnosing apparatus and the like in a medical field is used herein. The method is called digital scan converter (hereinafter abbreviated to "DSC").

The function of the DSC is to convert a ultrasonic image according to any one of various scan scanning method thereby display the image on a TV monitor. This function is attained by the steps of: digitalizing ultrasonic echo by use of the A/D converter 45; writing the digital signal in a frame memory 36 in accordance with a ultrasonic scanning method (In this embodiment, the method is called "linear scan". Other scanning methods include "sector scan" and the like.); and reading the data from the frame memory 36 in accordance with a TV scanning method. (The data are converted into analog data by D/A conversion when the data are read out.)

On the other hand, when the switching circuit 35 is in a state of C-scope display, the output signal is connected to the gate circuit 50. A C-scope image can be obtained by applying a gate signal G from the gate circuit 50 to the Rf waveform RF as shown in the Diagrams (A) and (B) of FIG. 16.

The gate circuit 50 has polarity switching over means for selecting one from the two of positive (+) and negative (−). When positive (+) is selected, an analog (direct-current) voltage proportional to the maximum value ($V_p$) of the positive side of the waveform in the gate is generated. When negative (−) is selected, an analog (direct-current) voltage proportional to the maximum value ($V_n$) of the negative side thereof is generated. The analog output is converted into a digital signal at every sampling pitch to thereby be transmitted to a predetermined address in the frame memory 36.

As described above, according to the embodiment shown in FIGS. 14 to 16, switching means such as a switching circuit is provided so that a B-scope image can be formed in a desired position after a C-scope image is formed. Because the C-scope image (horizontal sectional image) and the B-scope image (vertical sectional image) can be displayed at once, more detailed inspection can be made. Further, because the position of B-scope display is very exact, the real position of the flaw in the object can be found exactly.

As described above, according to the present invention, a cursor can be displayed on a screen of display of a ultrasonic image obtained by scanning the surface of an object to be inspected by use of a probe formed by arrangement of array elements and, further, the cursor can be moved to a desired position of the ultrasonic image so that ultrasonic waves are emitted to a position of the surface of the object corresponding to the aforementioned position and the reflected wave signals are displayed in another display portion. Accordingly, not only supersonic flaw detection (C-scope) on a plane of the object can be conducted, but also ultrasonic flaw detection (A-scope and B-scope) in the direction of depth in a desired position of the object can be conducted. Consequently, detailed analysis of the flaw portion can be made.

I claim:

1. An ultrasonic flaw detecting system comprising:
   an array probe constituted by a large number of array elements arranged in a direction of a first axis for serving transmission and reception of ultrasonic waves;
   switching means for switching said array elements so as to successively select a predetermined number of ones of said array elements on the basis of a clock signal;
   moving means for moving said array probe in a direction of a second axis orthogonal to said first axis;
   delay control means provided for both transmission and reception of ultrasonic waves for the double purpose of converging ultrasonic waves at a predetermined point and receiving reflection waves from said point;
   a display portion for displaying an ultrasonic image in a plane formed by said first and second axes on the basis of signals received by said array elements;
   cursor display means for displaying a cursor in said display portion;
   computing means for computing the amount of movement of said cursor;
   clock signal output control means for generating said clock signal having a number of pulses corresponding to the amount of movement of said cursor in said first axial direction;
   driving means for driving said moving means corresponding to the amount of movement of said cursor in the second axial direction; and
   a second display portion for displaying an ultrasonic image in a direction of a third axis orthogonal to said first and second axes.

2. An ultrasonic flaw detecting system comprising:
   an array probe constituted by a large number of array elements arranged in a direction of a first axis for serving transmission and reception of ultrasonic waves;
   switching means for switching said array elements so as to successively select a predetermined number of ones of said array elements on the basis of a clock signal;
   moving means for moving said array probe in a direction of a second axis orthogonal to said first axis;
   delay control means provided for both transmission and reception of ultrasonic waves for the double purpose of converging ultrasonic waves at a predetermined point and receiving reflection waves from said point;
   a display portion for displaying an ultrasonic image in a plane formed by said first and second axes on the basis of signals received by said array elements;
   cursor display means for displaying a cursor in said display portion;
   computing means for computing the amount of movement of said cursor;
   clock signal output control means for generating said clock signal having a number of pulses corresponding to the amount of movement of said cursor in said first axial direction;
   driving means for driving said moving means corresponding to the amount of movement of said cursor in the second axial direction; and
   a second display portion for displaying an ultrasonic image in a direction of a third axis orthogonal to said first and second axes, so that said system is capable of simultaneously conducting plan-image display (B-scope display).

3. An ultrasonic flaw detecting system according to claim 2, in which said plane-image display includes a switching circuit for switching reception waves from said array probe, a detection circuit for detecting the signal thus selected by said switching circuit, and a frame memory for storing the thus detected signal therein.

4. An ultrasonic flaw detecting system according to claim 2, in which said sectional-image display includes a switching circuit for switching reception waves from said array probe, a gate circuit for getting the signal thus selected by said switching circuit, and a frame memory for storing the output of said gate circuit therein.

5. An ultrasonic flaw detecting system comprising:
   an array probe constituted by a large number of array elements arranged both in a direction of a first axis and in a direction of a second axis orthogonal thereto for serving transmission and reception of ultrasonic waves;
   switching means for switching said array elements so as to successively select a predetermined number of ones of said array elements on the basis of a clock signal;
   delay control means provided for both transmission and reception of ultrasonic waves for the double purpose of converging ultrasonic waves at a predetermined point and receiving reflection waves from said point;

a display portion for displaying an ultrasonic image in a plane formed by said first and second axes on the basis of signals received by said array elements;

cursor display means for displaying a cursor in said display portion;

computing means for computing the amounts of movement of said cursor in said first and second axial direction;

clock signal output control means for generating said clock signal having a number of pulses corresponding to the amount of movement of said cursor in said first axial direction and for generating said clock signal having a number of pulses corresponding to the amount of movement of said cursor in said second axial direction; and a second display portion for displaying an ultrasonic image in a direction of a third axis orthogonal to said first and second axes, so that said system is capable of simultaneously conducting plane-image display (C-scope display) and sectional-image display (B-scope display).

6. An ultrasonic flaw detecting system according to Claim 5, in which said plane-image display includes a switching circuit for switching reception waves from said array probe, a detection circuit for detecting the signal thus selected by said switching circuit, and a frame memory for storing the thus detected signal therein.

7. An ultrasonic flaw detecting system according to Claim 5, in which said sectional-image display includes a switching circuit for switching reception waves from said array probe, a gate circuit for gating the signal thus selected by said switching circuit, and a frame memory for storing the output of said gate circuit therein.

* * * * *